US00PP21572P2

(12) United States Plant Patent
Verboom

(10) Patent No.: US PP21,572 P2
(45) Date of Patent: Dec. 14, 2010

(54) ***MAHONIA* PLANT NAMED 'CABARET'**

(50) Latin Name: ***Mahonia* hybrid**
Varietal Denomination: Cabaret

(75) Inventor: Klaas Willem Verboom, Boskoop (NL)

(73) Assignee: Valkplant BV, Boskoop (NL)

( * ) Notice: Subject to any disclaimer, the term of this patent is extended or adjusted under 35 U.S.C. 154(b) by 0 days.

(21) Appl. No.: 12/655,655

(22) Filed: Jan. 5, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Penny J Aguirre

(57) ABSTRACT

A new cultivar of hybrid *Mahonia,* 'Cabaret', characterized by its late bloom season flowering from late August/early September to mid November in The Netherlands, its compact plant habit, and its orange-red flower buds followed by red berries.

2 Drawing Sheets

Botanical classification: *Mahonia* hybrid.
Variety denomination: 'Cabaret'.

BACKGROUND OF THE INVENTION

The present invention relates to a new and distinct cultivar of *Mahonia*, botanically of hybrid origin. The new cultivar will be referred to hereafter by its cultivar name, 'Cabaret'. 'Cabaret' is an evergreen shrub grown for use as a landscape plant.

The Inventor discovered 'Cabaret' as a naturally occurring whole plant mutation in fall of 2004 in a trial bed in Boskoop, The Netherlands. An unnamed plant of *Mahonia nitens* and an unnamed plant of *Mahonia gracilipes* are considered by the Inventor to be the most likely parents based on the characteristics of 'Cabaret' and its close proximity in the trial bed.

Asexual reproduction of the new cultivar was first accomplished by the Inventor using softwood stem cuttings in December of 2002 in Booskoop, The Netherlands. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial garden for ten years in Boskoop, The Netherlands. These attributes in combination distinguish 'Cabaret' as a unique cultivar of *Mahonia.*

1. 'Cabaret' blooms from late August/early September to mid November in The Netherlands.
2. 'Cabaret' has a compact plant habit.
3. 'Cabaret' exhibits orange-red flower buds followed by red berries.

'Cabaret' can be most closely compared its probably parent plants. 'Cabaret' differs from *Mahonia nitens* in flowering early in the season as *Mahonia nitens* blooms from mid August to late October/early November. In addition, the plant habit of *Mahonia nitens* is less compact. *Mahonia gracilipes* differs from 'Cabaret' in being more vigorous and in having leaves with more spines that are sharper. There are no cultivars of *Mahonia* known to the Inventor that are similar to the new cultivar.

BRIEF DESCRIPTION OF THE DRAWING

The accompanying colored photographs illustrate the overall appearance and distinct characteristics of a 2 year-old plant of the new *Mahonia* as grown outdoors in a 3-liter container in Booskoop, The Netherlands.

The photograph on the first sheet provides a side view of 'Cabaret' in bloom and illustrates the overall appearance and plant habit.

The photograph on the top of the second sheet provides a close-up view of the flowers and flower buds of 'Cabaret'.

The photograph on the bottom of the second sheet provides a close-up view of the foliage of 'Cabaret'. The colors in the photographs are as close as possible with the digital photography techniques available, the color values cited in the detailed botanical description accurately describe the colors of the new *Mahonia.*

DETAILED BOTANICAL DESCRIPTION

The following is a detailed description of 2 year-old plants the new *Mahonia* as grown outdoors in 3-liter containers in Boskoop, The Netherlands. Plants were grown under average day temperatures of 10° to 20° C. and average night temperatures of 2° to 12° C. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—Blooms from late August/early September to mid November.

*Plant habit.*—Evergreen shrub, broadly upright, compact habit.

*Height and spread.*—Reaches about 90 cm in height and width after 6 years, a 2 year-old plant reached about 27 cm in height (in bloom) and 31 cm in width.

*Cold hardiness.*—At least to U.S.D.A. Zone 7.

*Diseases and pests.*—No susceptibility or resistance to diseases or pests has been observed.

*Root description.*—Fleshy.

Growth and propagation:

*Propagation.*—Terminal, softwood stem cuttings.

*Growth rate.*—Slow, grows about 10 cm per season.

Stem description:

*Shape.*—Round.

*Stem color.*—New growth emerges 146B, maturing to N199A to N199B striped with 197A to 197B.

*Stem size.*—An average of 9.3 cm in length and 5 mm in diameter.

*Stem surface.*—Glabrous, very slightly glossy.

*Internode length.*—An average of 4 mm, leaves are clustered on upper portion of the branches.

*Stem strength.*—Strong.

*Branching.*—Basal branching with an average of 3 on a plant 2 years in age.

Foliage description:

*Leaf shape.*—Narrow oblong.

*Leaf division.*—Imparipinnate (odd-pinnate).

*Leaf base.*—Obtuse (leaf and leaflets).

*Leaf apex.*—Sharply acute (leaf and leaflets) with apex of leaflets pointed downwards.

*Leaf fragrance.*—None.

*Leaflet venation.*—Pinnate, Color; upper surface 144B, lower surface 146A.

*Leaflet margins.*—Spiny-serrate with 3 serrations per side.

*Leaf arrangement.*—Whorls to alternate, leaflets are opposite.

*Leaf attachment.*—Rachis sheathed to stem, leaflets sessile.

*Leaf surface.*—Glabrous and glossy on upper surface, glabrous on lower surface.

*Leaf size.*—Average of 15.6 cm in length and 5.3 cm in width.

*Leaflet size.*—Average of 4.1 cm in length and 2.4 cm in width.

*Leaflet internode length.*—An average of 2.4 cm.

*Leaf quantity.*—Average of 7 leafs per branch.

*Leaflet quantity.*—11 leaflets per leaf.

*Leaf color.*—Newly expanded leaves; upper surface 152A, lower surface a color between 176B and 178A, mature leaves; upper surface a color between N137D and 147A, lower surface 146B.

*Rachis.*—Round, about 11.4 cm in length, 1.5 cm in diameter, surface is slightly lustrous, color on young leaves is 183B on upper surface and 174A on lower surface, color on mature leaves 144A.

*Leaf spines.*—An average of 4 mm in length, 196A in color at tip.

Inflorescence description:

*Inflorescence type.*—Fascicles of racemes arranged in whorls emerging above leaf whorls, flowers open from bottom of raceme towards apex, racemes of tightly packed cup-shaped flowers.

*Inflorescence size.*—Racemes an average of 10.3 cm in length and 1.5 cm in diameter.

*Flower buds.*—Flattened globular in shape, an average of 3.5 mm in length and 4 mm in width, color ranges from N34 to 172A.

*Flower fragrance.*—Faintly sweet-scented.

*Lastingness of flower.*—About 7 days, not persistent.

*Flower quantity.*—About 50 flowers per raceme, about 600 flowers per plant.

*Flower type.*—Perfect, cup-shaped, single.

*Flower aspect.*—Outward to slightly upright.

*Flower size.*—Average of 8 mm in diameter and 4 mm in depth.

*Peduncles.*—An average of 9.9 cm in length and 2 mm in diameter, 146A to 146B in color, held upright to a 30° angle from the stem.

*Pedicels.*—About 4 mm in length and 0.75mm in diameter, 146A to 147A in color, held at about a 35° angle from peduncle.

*Flower buds.*—Flattened globular in shape, up to 4 mm in diameter, N34 to 172A in color.

*Petals.*—6, un-fused, broadly ovate in shape and concave, upper and lower surface is smooth and glabrous, entire margin, square base, retuse apex, about 3 cm in length and 2 mm in width, color is 4B when opening and mature (lower and upper surface).

*Calyx.*—Cup-shaped, an average of 4 mm in length and 8 mm in diameter.

*Sepals.*—6, ovate in shape, strongly concave, glabrous surface, about 4 mm in length and 3 mm in width, entire margin, broadly acute apex and broadly cuneate base, lower surface in 26A to 31A when opening and 26A to 26B when mature, upper surface is 26B when opening and 26B to 26C when mature.

Reproductive organs:

*Gynoecium.*—1 pistil, about 0.2 mm in length, style absent, stigma is sessile to ovary and 151C to 151D in color, ovary is superior and 144C in color.

*Androcoecium.*—6 stamens, filaments are about 1.5 mm in length, anthers are oblong in shape, 1.5 mm in length and 0.75 mm in width and 4B in color, pollen is low in quantity and 4D in color.

*Fruit and seed.*—Berry; globose in shape, about 8 mm in length and width, smooth and glossy surface, seed; an average of 3 per fruit, an average of 5 mm in length and 3 mm in diameter, 165C in color.

It is claimed:

1. A new and distinct cultivar of *Mahonia* plant named 'Cabaret' as herein illustrated and described.

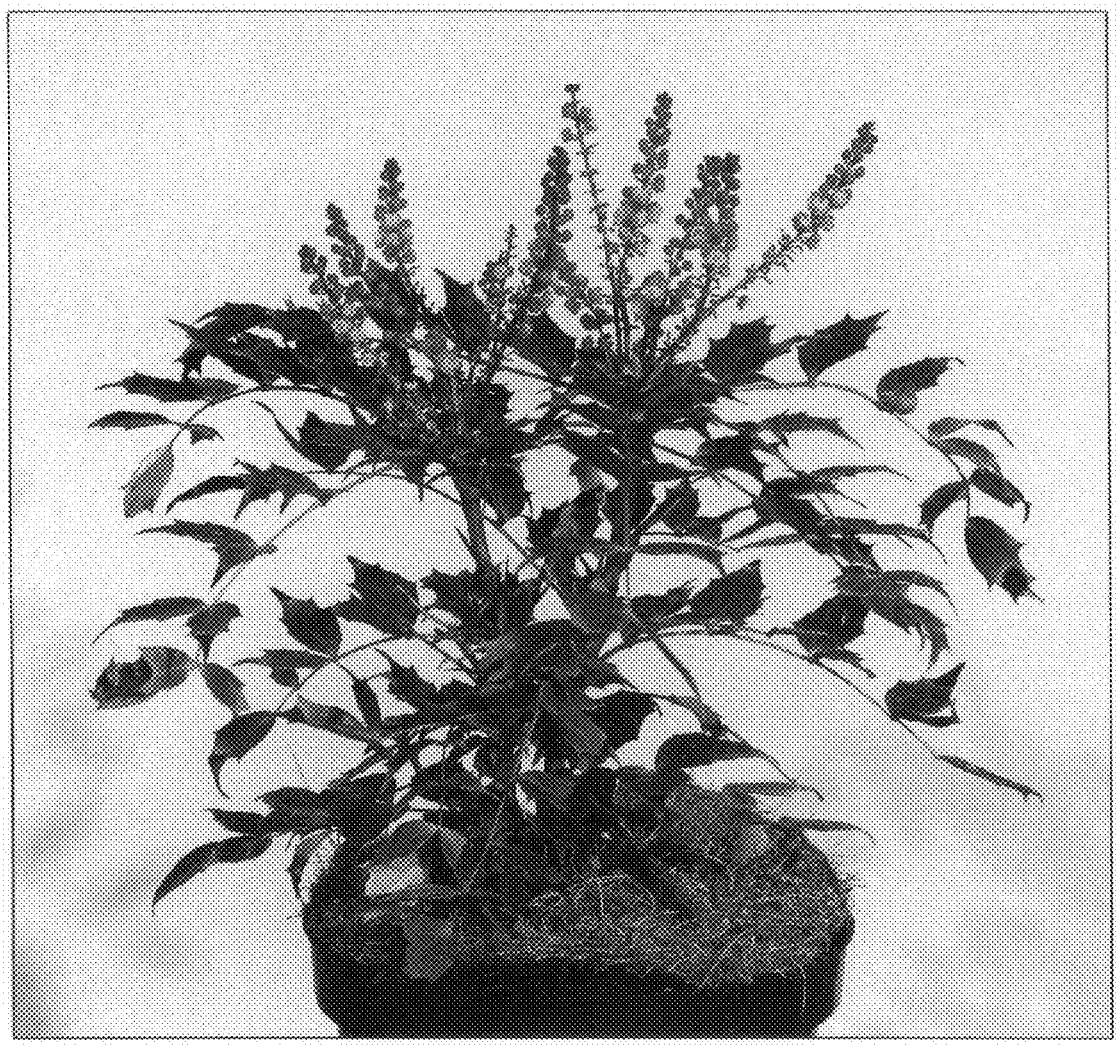

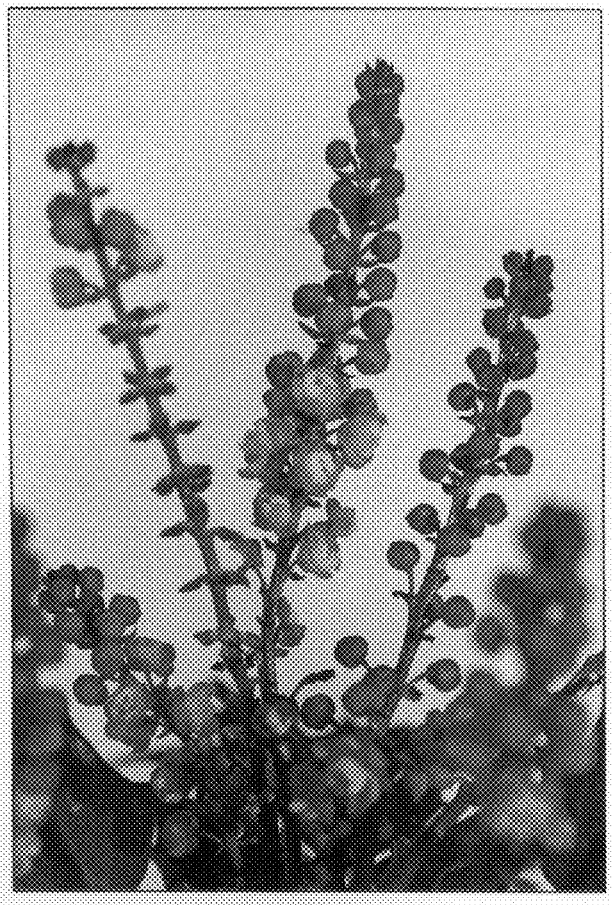
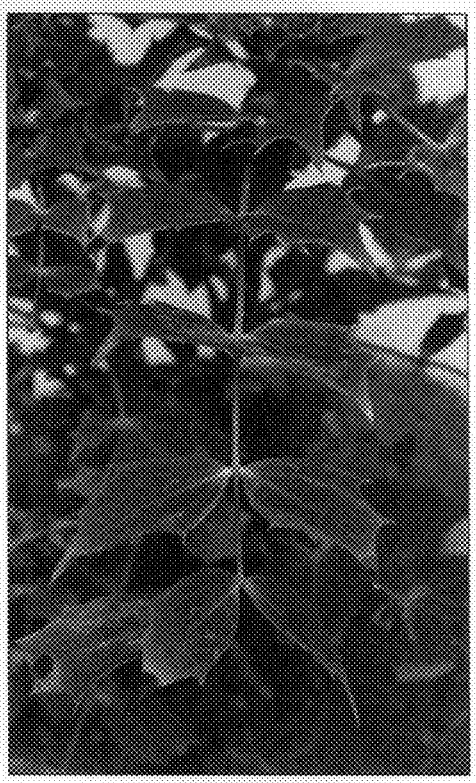

* * * * *